United States Patent
Lin et al.

(10) Patent No.: US 8,197,849 B2
(45) Date of Patent: Jun. 12, 2012

(54) CROSS-LINKED OXIDATED HYALURONIC ACID FOR USE AS A VITREOUS SUBSTITUTE

(75) Inventors: Feng-Huei Lin, Miaoli County (TW); Wen-Yu Su, Miaoli County (TW); Yu-Chun Chen, Miaoli County (TW); Ko-Hua Chen, Taipei (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/871,923

(22) Filed: Aug. 31, 2010

(65) Prior Publication Data

US 2011/0200676 A1 Aug. 18, 2011

Related U.S. Application Data

(60) Provisional application No. 61/303,673, filed on Feb. 12, 2010.

(51) Int. Cl.
*A61K 9/14* (2006.01)
*A61K 31/765* (2006.01)
*A61F 2/00* (2006.01)

(52) U.S. Cl. ...... 424/488; 424/427; 424/428; 424/78.38

(58) Field of Classification Search .......... 424/427, 424/428, 488, 78.38
See application file for complete search history.

(56) References Cited

U.S. PATENT DOCUMENTS

| 4,716,154 A | 12/1987 | Malson et al. |
| 5,258,412 A | 11/1993 | Peyman |
| 5,874,417 A | 2/1999 | Prestwich et al. |
| 6,969,531 B2 * | 11/2005 | Dehazya et al. ............ 424/493 |

FOREIGN PATENT DOCUMENTS

| EP | 1129683 A1 | 9/2001 |
| WO | 2006/130455 A2 | 12/2006 |

OTHER PUBLICATIONS

Soman et al. ("Articficial Vitreous Replacements," in Bio-Medical Materials and Engineering 13, (2003), 59-74).*
Kanski ("Intracitreal hyaluronic acid injection," in Brit. J. Ophthal. (1975), 59, 255, 256).*
Kummer et al. "Artificial Vitreous Humor for In Vitro Experiments" in the Proceedings of the 29th Annual International Conference of the IEEE EMBS, Aug. 23-26, 2007.*
Pruett et al. "Hyaluronic Acid Vitreous Substitute," in Arch Ophthalmol. 1979;97(12):2325-2330 (Abstract).*
Su et al. (Injectable oxidized hyaluronic acid/adipic acid dihydrazide hydrogel for nucleus pulposus regeneration in Acta Biomaterialla, 6 (20100, pp. 3044-3055) published Mar. 1, 2010.*

(Continued)

*Primary Examiner* — Blessing Fubara
(74) *Attorney, Agent, or Firm* — Hsiu-Ming Saunders; Intellectual Property Connections, Inc.

(57) ABSTRACT

A composition comprising a polymer that comprises oxidated hyaluronic acid cross-linked by a dihydrazide is disclosed. The polymer is a hydrogel exhibiting the following properties: a) transparent and colorless; and b) transforming from a liquid state into a gel-matrix at 37° C. These characteristics make it useful as a vitreous humor substitute.

20 Claims, 9 Drawing Sheets

OTHER PUBLICATIONS

Xiaodong Shen et al. (2009) "Coronary Arteries Angiogenesis in Ischemic Myocardium: Biocompatibility and Biodegradability of Various Hydrogels" Artificial Organs 33(10):781-787.

Xinqiao Jia et al. (2004) "Synthesis and Characterization of in Situ Cross-Linkable Hyaluronic Acid-Based Hydrogels with Potential Application for Vocal Fold Regeneration" Macromolecules 37, 3239-3248.

Kuen Yong Lee at al. (2004) "Controlled degradation of hydrogels using multi-functional cross-linking molecules" Biomaterials 25, 2461-2468.

João MaiaJo et al. (2005) "MaiaSynthesis and characterization of new injectable and degradable dextran-based hydrogels" Polymer 46, 9604-9614.

* cited by examiner hyaluronic acid (HA)   Oxidized hyaluronic acid (oxi-HA)

A

B

CROSS-LINKED OXIDATED HYALURONIC ACID FOR USE AS A VITREOUS SUBSTITUTE

REFERENCE TO RELATED APPLICATION

The present application claims the priority to U.S. Provisional Application Ser. No. 61/303,673, filed Feb. 12, 2010, which is herein incorporated by reference in its entirety.

FIELD OF THE INVENTION

The present invention relates generally to vitreous replacements, and more specifically to vitreous humor substitutes, method of making and using the same.

BACKGROUND OF THE INVENTION

The vitreous body is a clear, transparent gelatinous substance in the vitreous cavity of the eye that is posterior to the lens and anterior to the retina. It occupies two thirds of the ocular volume; with a weight of approximately 4 g and a volume of about 4 ml. The main components of vitreous body include water (98%), collagen fibrils, glycosaminoglycans, hyaluronic acid (HA) and other rest solutes. Specific diseases, age-related degeneration or trauma can lead to pathological changes in the vitreous body, including HA degeneration and collagen precipitation, which result in liquefaction of the matrix. A degenerated or liquefied vitreous body will lead to floater formation and eventually result in posterior vitreous detachment and possible retinal detachment.

Among clinical treatments, pars plana vitrectomy (PPV) is one of the most important surgeries for treating a number of ocular-related diseases, including diabetic retinopathy, complex retinal detachment (for example, due to trauma) and macular hole. During PPV, the vitreous body is cut and aspirated, and then is typically replaced with a vitreous substitute, such as gas (air, perfluoropropane or sulfur hexafluoride) or silicone oil. Vitreous substitutes are used to fill vitreous cavity and help reattach the retina after vitrectomy surgery. Postoperatively, a vitreous substitute can keep the retina in position while the adhesion between the retina and the retinal pigment epithelium (RPE) cells forms. Gases, which are lighter than water, are useful for flattening a detached retina and keeping it attached while healing occurs. However, it is frequently necessary to maintain a face-down position following surgery for a week or more when gas is used. Silicone oil is sometimes used instead of gases to keep retina attached postoperatively since 1960s for complicated retinal detachments, or in patients unable to position postoperatively (e.g. children), but long-term complications can occur if the silicone oil is not removed later. Besides, silicone oil also may be cytotoxic to ocular tissues, such as corneal endothelial cells.

Recently, numerous vitreous substitute materials using natural, semi-synthetic or synthetic polymer have been investigated, including poly(vinyl alcohol), poly(1-vinyl-2-pyrrolidone), poly(acrylamide), poly(glyceryl methacrylate), poly(methyl-2-acrylamido-2-methoxyacetate) and poly(2-hydroxyethylacrylate). Criteria for the ideal vitreous substitute include clarity, transparency, refractive index, sufficient rigidity to act as a tamponade substitute, ability to allow metabolite transfer, non-absorbable characteristics, hydrophilic composition and the ability to be injected through a small-gauge needle. These criteria suggest that finding a proper material for a vitreous substitute is not an easy task.

Therefore, a heretofore unaddressed need exists in the art to address the aforementioned deficiencies and inadequacies, especially in connection with vitreous substitutes.

SUMMARY OF THE INVENTION

In one aspect, the invention relates to a composition comprising a polymer, the polymer comprising oxidated hyaluronic acid cross-linked by a dihydrazide; wherein the polymer is a hydrogel exhibiting the following properties: a) transparent and colorless; and b) transforming from a liquid state into a gel-matrix at 37° C.

In another aspect, the invention relates to a method of preparing a composition as aforementioned, comprising admixing a first solution comprising oxidated hyaluronic acid with a second solution comprising a dihydrazide to form a composition comprising a polymer comprising oxidated hyaluronic acid cross-linked by a dihydrazide.

Further in another aspect, the invention relates to a kit comprising: a) oxidated hyaluronic acid; b) a dihydrazide; c) buffer; and d) an insert with instructions on preparing a composition as aforementioned.

Further in another aspect, the invention relates to a method of replacing the vitreous of an eye comprising: removing the vitreous from a vitreous cavity of an eye; replacing vitreous with air; and injecting an amount of a composition as aforementioned into the vitreous cavity, the amount of the composition being sufficient to replace the air.

Yet in another aspect, the invention relates to a composition comprising a cross-linked polymer of formula (I):

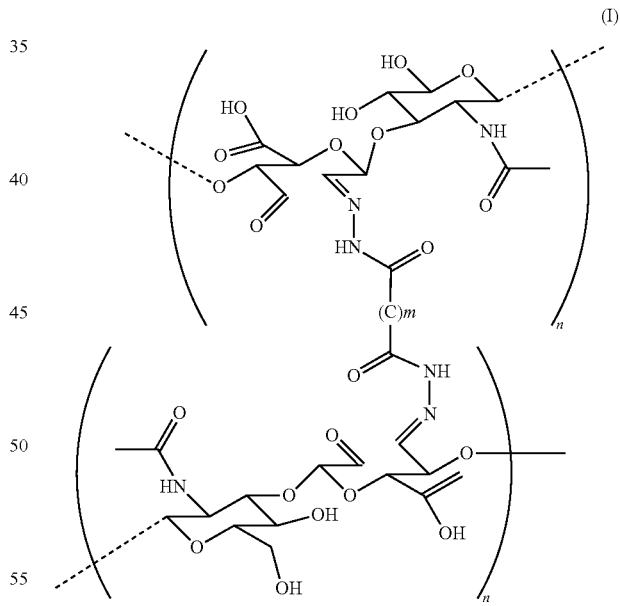

(I)

wherein m, n are integers, m≦5, 100≦n≦2500; and wherein the polymer is a hydrogel exhibiting the following properties: a) transparent and colorless; and b) transforming from a liquid state into a gel-matrix within 5 minutes at 37° C.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
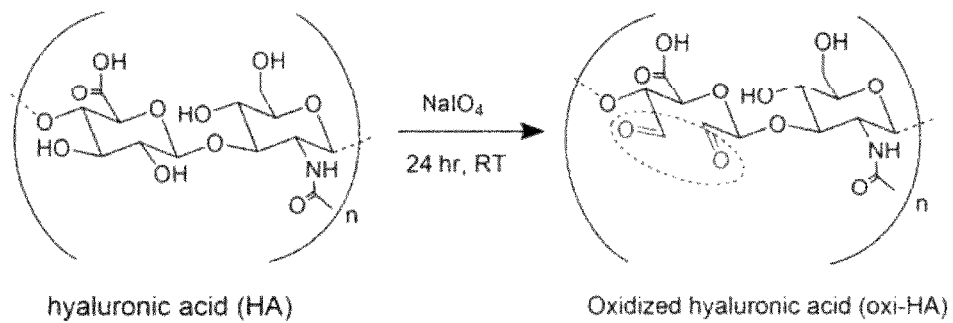
FIG. 1A shows hyaluronic acid (HA) is oxidized by sodium periodate ($NaIO_4$).

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

The term "hydrogel," as used herein, refers to a cross-linked network of hydrophilic polymers.

Dihydrazides are represented by the active group:

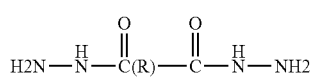

where R is can be any polyvalent organic radical preferably derived from a carboxylic acid. Carboxylic acid esters are reacted with hydrazine hydrate in an alcohol solution using a catalyst and a water extraction step. The most common dihydrazides include adipic acid dihydrazide (ADH), derived from adipic acid, sebacic acid dihydrazide (SDH), valine dihydrazide (VDH), derived from the amino acid valine, and isophthalic dihydrazide (IDH). The aliphatic R group can be of any length. For example, when R group is just carbon, the resulting compound is carbodihydrazide (CDH), the fastest dihydrazide. Or R as long as C-18 has been reported as in icosanedioic acid dihydrazide (LDH). The safety of ADH has been well established.

The invention relates to an injectable, in-situ-formed hydrogel that is composed of oxidated HA (oxi-HA) and adipic acid dihydrazide (ADH) as a vitreous substitute. As described previously, HA is one of the major components of the vitreous humor. It has been used broadly in the area of biomaterials, tissue engineering and other related fields. These glucose-based polymers contain a high density of hydroxyl groups that make the polymers highly hydrophilic and further chemically functionalized. Hyaluronic acid was first used as vitreous substitute in 1960s. However, hyaluronic acid does not provide appropriate tamponading effect on the retina during surgery or afterwards, partly because of its low surface tension and its specific gravity. Besides, HA solutions have been shown not useful as long-term vitreous substitute because of their relatively rapid elimination from eye. To improve the retention time of HA-based vitreous substitutes, sodium periodate ($NaIO_4$) was used to oxidate HA to create aldehyde functional groups. Then, oxi-HA was cross-linked by ADH to form a clear, colorless and transparent oxi-HA/ADH hydrogel.

The aldehyde functional groups of oxi-HA were characterized by Fourier-Transformed Infrared (FT-IR) analysis and the degree of oxidation of oxi-HA was determined by trinitrobenzene sulfonic acid (TNBS) assay. Because an refractive index (RI) is an essential characteristic of vitreous substitutes, the RI of oxi-HA/ADH hydrogels with various compositions were measured by a refractometer. The gelation properties of oxi-HA/ADH hydrogels were evaluated by rheological analysis at 4° C. and 37° C. The elastic (G') and viscous (G") moduli were recorded to determine the gelation time. In addition, in-vitro degradation time, swelling properties and cytotoxicity of oxi-HA/ADH were also investigated.

In one aspect, the invention relates to a composition comprising a polymer, the polymer comprising oxidated hyaluronic acid cross-linked by a dihydrazide; wherein the polymer is a hydrogel exhibiting the following properties: a) transparent and colorless; and b) transforming from a liquid state into a gel-matrix at 37° C.

In one embodiment of the invention, the hydrogel transforms from a liquid state into a gel within 5 minutes at 37° C.

In one embodiment of the invention, the dihydrazide is selected from the group consisting of adipic acid dihydrazide, oxalyldihydrazide, succinic dihydrazide, malonic dihydrazide, ethylmalonic acid, dihydrazide, sebasic acid dihydrazide, isophthalic acid dihydrazide, Ajicure LDH, Ajicure VDH, maleic acid dihydrazide and pimelic acid dihydrazide. For example, the polymer may comprise oxidated hyaluronic acid cross-linked by adipic acid dihydrazide.

In another embodiment of the invention, the cross-linked, oxidated hyaluronic acid of the polymer comprises glucuronic acids with C2 or C3 or both thereof being aldehyde groups.

In another embodiment of the invention, the dihydrazide cross-links two chains of oxidated HA via C2 and C3 of glucuronic acids of the oxidated HA.

In another embodiment of the invention, the cross-linked, oxidated hyaluronic acid in the polymer comprises glucuronic acids with C2 or C3 or both thereof being oxidated.

In another embodiment of the invention, the weight ratio between the oxidated HA and hydrazide ranges from 12:1 to 3:1. Without intent to limit the scope of the invention, an example of the weight ratio between the oxidated HA and adipic acid dihydrazide is 3:1.

In another embodiment of the invention, the composition has a refractive index ranging from 1.341 to 1.345.

In another embodiment of the invention, the composition has a refractive index ranging from 1.3420 to 1.3442.

In another aspect, the invention relates to a method of preparing a composition as aforementioned, comprising admixing a first solution comprising oxidated hyaluronic acid with a second solution comprising a dihydrazide to form a composition comprising a polymer comprising oxidated hyaluronic acid cross-linked by a dihydrazide.

In one embodiment of the invention, the concentration of oxidated hyaluronic acid in the first solution is greater than 4% but less than (w/v) 8%, and wherein the concentration of dihydrazide in the second solution ranges from 2 to 8%.

In another embodiment of the invention, the weight or concentration ratio of oxidated hyaluronic acid and dihydrazide in the composition is 3:1.

In another embodiment of the invention, the weight or concentration ratio of oxidated hyaluronic acid and ADH in the composition is from 3:1 to 12:1.

In another embodiment of the invention, the admixing step is performed at a temperature that forms a polymer having a gelation time of no less than 5 minutes.

Further in another aspect, the invention relates to a kit comprising: a) oxidated hyaluronic acid; b) a dihydrazide; c) buffer; and d) an insert with instructions on preparing a composition as aforementioned.

In one embodiment of the invention, the dihydrazide in the aforementioned kit is adipic acid dihydrazide.

Further in another aspect, the invention relates to a method of replacing the vitreous of an eye comprising:
removing the vitreous from a vitreous cavity of an eye;
replacing vitreous with air; and
injecting an amount of a composition as aforementioned into the vitreous cavity, the amount of the composition being sufficient to replace the air.

Yet in another aspect, the invention relates to a composition comprising a cross-linked polymer of formula (I):

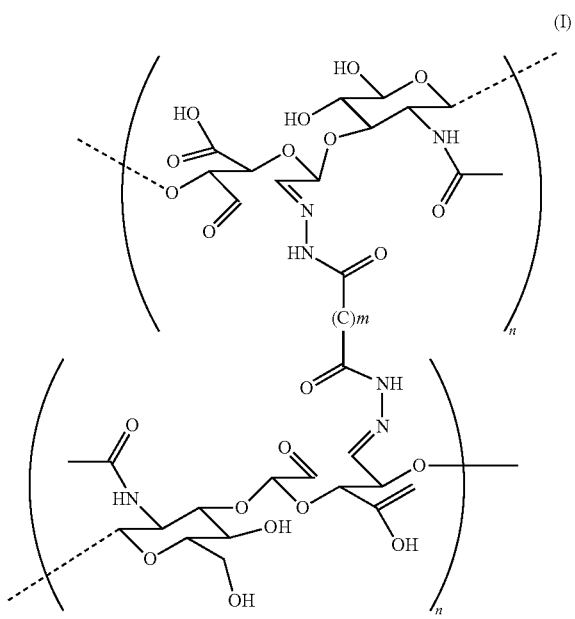

(I)

wherein m, n are integer, m≦5, 100≦n≦2500;
and wherein the polymer is a hydrogel exhibiting the following properties:
transparent and colorless; and
transforming from a liquid state into a gel-matrix at 37° C.

In one embodiment of the invention, m=4.

In another embodiment of the invention, n is ≦2400, ≦2300, ≦2200, ≦2100, ≦2000, ≦1900, ≦1800, ≦1700, ≦1600, ≦1500, ≦1400, ≦1300, ≦1200, ≦1100, or ≦1000.

In another embodiment of the invention, n≧200, ≧300, ≧400, ≧500, ≧600, ≧700, ≧800, or ≧900.

In another embodiment of the invention, the oxidated HA in the polymer of the composition has a theoretical degree of oxidation at least 40%, 45%, 50%, 55%, 60%, 65%, 70%, 75%, 80%, 85%, 90%, 95%, or 100%.

In another embodiment of the invention, the oxidated HA in the composition has an experimental degree of oxidation at least 20%, 25%, 30%, 35%, 40%, 45%, 50%, 55%, 60%, 65%, 70%, 75%, 80%, 85%, 90%, 95%, or 100%.

In another embodiment of the invention, the oxidated HA has a theoretical degree of oxidation of 100% and/or an experimental degree of oxidation ranging from 20% to 80%.

In another embodiment of the invention, the oxidated HA in the polymer of the composition has a degree of oxidation at least 40%, 45%, or 50%.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods 2.1 Materials

Hyaluronic acid (average molecular weight of $3.2 \times 10^5$ Da) was purchased from Q.P. Corporation (Tokyo, Japan). Sodium tetraborate decahydrate (borax), tert-butyl carbazae and adipic acid dihydrazide were purchased from Sigma-Aldrich (St. Louis, Mo., USA). Diethyleneglycol, potassium bromide (kBr), and sodium periodate ($NaIO_4$) were purchased from RDH Chemical Co (Spring valley, CA, USA). Trichloroacetic acid was purchased from JTB Corporation (Tokyo, Japan). Dialysis tube (MWCO 6,000-8,000) was from Membrane Filtration Products Inc (Texas, USA). Human retina pigmented epithelium cells (RPE cells, BCRC 60383) were supplied from National Centre for Cell Sciences, Taiwan. Cell-culture medium DMDM/F-12, trypsin-EDTA, fetal bovine serum, and penicillin-streptomycin were purchased from Gibco (Grand Island, N.Y., USA). Quick Cell Proliferation Assay Kit II was from BioVision Inc. (CA, USA). CYTOTOX 96® Non-Radioactive Cytotoxicity Assay was from Promega Corporation (WI, USA). The Live/Dead Viability/Cytotoxicity kit for mammalian cells was from Molecular Probes (Eugene, Oreg., USA).

2.2. Preparation of Oxidated Hyaluronic Acid (oxi-HA)

Hyaluronic acid (HA) was oxidized by sodium periodate ($NaIO_4$) in an aqueous solution at room temperature for 24 hr. In a 300 ml beaker wrapped with aluminum foil, hyaluronic acid (2.00 g) was dissolved in double-distilled water (200 ml), and then various concentrations of sodium periodate solution were added gradually while stirring. The molar ratio of $NaIO_4$ to HA was 1:2, 1:1 and 1:0.5 to achieve various oxidation degrees (low, middle and high oxi-HA). After 24 hr of stirring, the reaction was stopped by the addition of ethylene glycol with further stirring for a half hour. The resulting solution was dialyzed by a dialysis tube with a MWCO 6,000-8,000 (CelluSep T2 Tubings, Uptima) for 3 days with double-distilled water. The water was changed at least three times during the dialysis process. Finally, the dialyzed solution was lyophilized by a freeze dryer (FDU-1100, EYELA Corp., Tokyo, Japan) for 3 days to yield a white fluffy product, oxidated hyaluronic acid (oxi-HA). The obtained oxi-HA was manually pressed into small pellets for FT-IR analysis (JASCO FTIR-4200 with ATR PRO450-S).

2.3. Determination of Degree of Oxidation

The degree of oxidation of the oxi-HA was quantified by measuring the number of aldehyde functional groups in the oxi-HA using t-butyl carbazate (t-BC). Carbazates are well known to react with aldehydes to form stable carbazones in a similar manner to hydrazone formation. Thus, the degree of oxidation of the oxi-HA was determined by measuring the residual t-BC after excess t-BC (25 µl, 30.0 mM in 1% aqueous trichloroacetic acid) had reacted with the aldehyde functional groups of the oxi-HA (25 µl, 0.6 w/v %) for 24 hr. Residual t-BC was determined by adding excess aqueous trinitrobenzene sulfonic acid (TNBS) solutions (500 µl, 6.0 mM) and measuring the absorbance of the complex (trinitrophenyl derivative) at 340 nm. Various concentrations of aqueous t-BC solutions were used as standards to obtain a calibration curve to identify un-reacted carbazates in the experimental samples.

2.4. Preparation of Oxi-HA/ADH Hydrogel

Oxi-HA samples with various degrees of oxidation were separately dissolved in phosphate buffer solution (pH 7.4) to a final concentration of 6 w/v % at room temperature overnight. The 2, 4 and 8 w/v % of adipic acid dihydrazide (ADH) solutions were prepared in phosphate buffer solution. Oxi-HA solution (400 µl) was mixed with 2, 4, and 8 w/v % of ADH solutions (100 µl) in an eppendorf which was plunged into a bath containing water and ice (close to 0° C.) to form hydrogel oxi-HA/ADH2, oxi-HA/ADH4 and oxi-HA/ADH8 hydrogels, respectively.

2.5. Refractive Index of oxi-HA/ADH Hydrogel

A refractometer (DR-Al ATAGO, Japan) was used to measure the refractive index (RI) of oxi-HA/ADH2, oxi-HA/ADH4 and oxi-HA/ADH8 hydrogels. In brief, an aliquot volume of liquid-state oxi-HA/ADH solution was moved to the refractometer prism with a pipette tip. The refractometer prism was incubated at 37° C. by an isothermal circuiting water bath. After waiting for 10 minutes for gelation, the refractive index (RI) of hydrogel was read from the digital screen.

2.6. Rheological Evaluation of Oxi-HA/ADH Hydrogel

A rheometer (HAAKE Rheostress 600, Thermo Fisher Scientific Inc.) with cone and plate geometry (1-C35/2 Ti) was used to evaluate the rheological properties of oxi-HA/ADH hydrogels at the preservation temperature 4° C. and body temperature 37° C. The temperature 4° C. was used to evaluate the operation time for surgeon to mixed oxi-HA/ADH solution and 37° C. was used to evaluate the gelation time of oxi-HA/ADH hydrogel. The oscillation time sweep mode was operated at 0.1 Hz, 10 Pa and terminated after 15 min to determine the gelation time of oxi-HA/ADH hydrogels. The elastic modulus G' and the viscous modulus G" were recorded and analyzed by RheoWin 3 software.

2.7. In-Vitro Degradation Experiments of Oxi-HA/ADH Hydrogel

The degradation properties of oxi-HA/ADH2, oxi-HA/ADH4 and oxi-HA/ADH8 hydrogels were evaluated by immersing the preformed hydrogel in PBS containing 10000 unit/ml lysozyme. Lysozyme was selected for use in the degradation model system due to it is an ocular enzyme known to attack the polysaccharide moieties. Briefly, oxi-HA and ADH in solution were mixed in an eppendorf, and 300 μl of the mixture (oxi-HA/ADH solution) were immediately moved into a cylinder mold and allowed to gel for 10 min and form a cylinder hydrogel with a diameter of 0.7-mm and a height of 0.8-mm. The cylinder shaped oxi-HA/ADH hydrogel was placed in a 24-well culture plate and 3 ml PBS containing lysozyme was added to each well. The initial hydrogel dry weight ($W_{id}$) was determined immediately after the hydrogel was formed. At regular intervals, the hydrogels were removed and lyophilized by a freeze drier for 72 hr. The dry weight ($W_d$) of oxi-HA/ADH hydrogels at different time point were weighed and the degradation percentage was calculated by $[(W_{id}-W_d)/W_{id}]$.

2.8. Swelling Experiments of Oxi-HA/ADH Hydrogel

The swelling index of oxi-HA/ADH2, oxi-HA/ADH4 and oxi-HA/ADH8 hydrogels were evaluated under the same condition as in vitro degradation experiments. The initial hydrogel weight ($W_i$) was determined immediately after the hydrogel formed and then placed into 24-well culture plate. At regular intervals, hydrogels were removed from the PBS containing lysozyme, blotted with filter paper to remove surface water, weighed ($W_t$) and returned to the same container (the buffer solution was replaced at each measurement). The swelling index was calculated from the ratio between $W_t$ and $W_i$.

2.9. Cytotoxicity Evaluation of Oxi-HA/ADH Hydrogel

Cytotoxicity evaluation of oxi-HA/ADH hydrogel was carried out by testing the extraction medium with a monolayer of human retina pigmented epithelium cells (RPE cells, BCRC 60383, National Centre for Cell Sciences, Taiwan) according to ISO standards. The extraction medium was prepared by incubating oxi-HA/ADH2, oxi-HA/ADH4, and oxi-HA/ADH8 hydrogel with standard culture medium (DMEM/F-12) at a 0.75 cm$^2$/ml extraction ratio for 72 hr at 37° C. Two hundred microliters of the extraction medium was tested on a monolayer of RPE cells. RPE cells were seeded onto 96 well culture plates at a cell density of 5×10$^3$ cells/well and fed with standard culture medium at 37° C. overnight. The standard culture medium was then replaced with the extraction medium. Groups in the experiment including control (standard culture medium), negative control (Al$_2$O$_3$ extraction medium), positive control (0.1% Triton X-100-containing medium), and experimental groups (oxi-HA/ADH2, oxi-HA/ADH4, and oxi-HA/ADH8 extraction medium) were tested in hexylicate (n=6). After incubation at 37° C. for 1 and 3 days, cell viability and cytotoxicity evaluations were quantitatively assessed using the Quick Cell Proliferation Assay Kit II (BioVision Inc.) and CYTOTOX 96® Non-Radioactive Cytotoxicity Assay (Promega Corporation), separately. RPE Cells treated with the extraction medium were also stained with LIVE/DEAD staining kit (Molecular Probes # L3224).

Quick Cell Proliferation Assay Kit II was used to evaluate cell viability. Cells were cultured for 1 and 3 days and culture medium was then discarded and replaced with 0.2 ml of water-soluble tetrazolium-8 (WST-8) working solution in each well. WST-8 can be reduced by dehydrogenase in living cells to produce a yellow colored product (formazan). After 2 hr of incubation, 100 μl of working solution was quantitatively assessed by spectrophotometer readout at 450 nm. The reference wavelength was 650 nm.

CYTOTOX® 96 Non-Radioactive Cytotoxicity Assay kit was used to evaluate cytotoxicity. The assay kit quantitatively measures lactate dehydrogenase (LDH), which is a stable cytosolic enzyme released upon cell lysis. After 1 and 3 days of cultivation, both culture medium and cell total lysis were measured for absorbance at 490 nm according to the assay manual. Extraction medium (without incubation with RPE cells) was also evaluated to serve as background. The cytotoxicity was calculated by the following equation:

$$\text{Cytotoxicity (\%)} = \frac{OD_{culture\ medium} - OD_{background}}{OD_{total\ lysis} + OD_{culture\ medium} - OD_{background}} \times 100\%.$$

2.10. Preliminary Animal Study

Six eyes of three New Zealand white rabbits (2.8-3.2 kg) were used. The surgeries were performed under general anesthesia with intramuscular injection of ketalar/Chanazine 2%. Under an operating microscope, a sclerotomy was created approximately 3 mm in left eyes with a surgical blade. The vitreous body was aspirated by 18-gague needles as much as possible and replaced with air. Then oxi-HA/ADH solution was injected into the vitreous cavity. After surgery, the eyes were treated with gentamicin (genticin, Roche) as antibiotic eyedrops and tetracyclin hydrochloride ophthalmic ointment 3 times a day for 1 week. The right eye was used as a control without any surgery. An ophthalmic table slit lamp (Topcon Medical Systems, Inc.) was used to observe and record the anterior segment and ocular media. Intraocular pressure (IOP) was measured by schiotz tonometer at 1, 5, 8, 12, 15 and 3 weeks postoperatively. Ultrasonic Pachymetry (DGH Technology, Inc) was used to measure the central cornea thinkness. Three weeks after operation, three rabbits were sacrificed. Both the right (control) and left (operated) eyes were harvested from these animals. The eyes were fixated with 10% formaldehyde solution and they were embedded in paraffin and stained with hematoxylin and eosin (HE stain) for a light microscope observation.

2.11. Statistical Analysis

All data are expressed as mean±standard deviation. Statistical differences between groups were tested using one-way analysis of variance (ANOVA). Statistical significance was set in advance to a probability level of 0.05.

3. Results 3.1. Characterization of Oxidated Hyaluronic Acid (Oxi-HA)

Figure 1B:
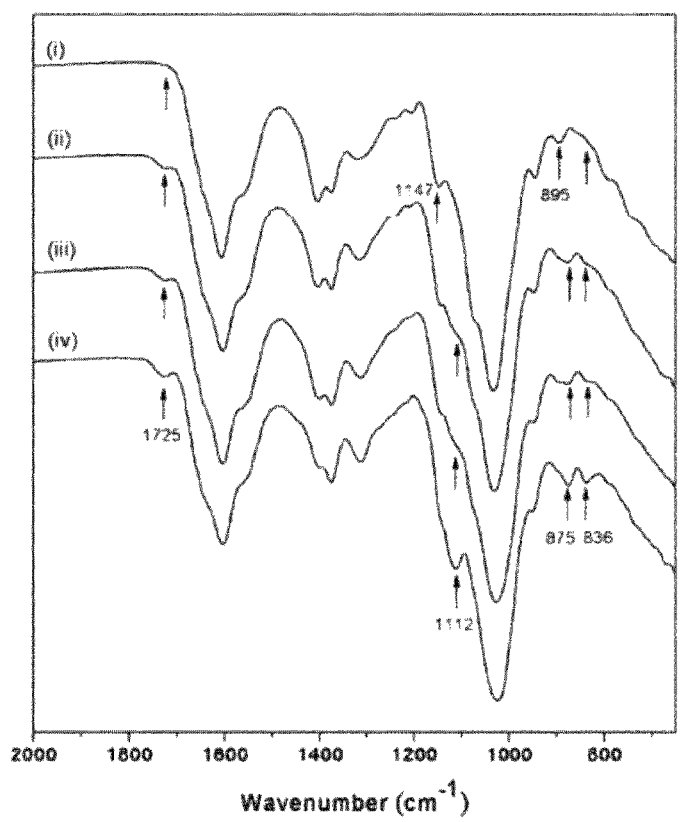
FIG. 1B is FTIR spectra of oxidated hyaluronic acid (oxi-HA) with different degrees of oxidation (DO): (i) HA power (DO: 0%), (ii) low oxi-HA (DO: 27.3%), (iii) middle oxi-HA (DO: 44.3%) and (iv) high oxi-HA (DO: 60.4%). The arrow indicates the aldehyde functional groups of oxi-HA at 1725 $cm^{-1}$ and 836 $cm^-$, and the shifting peaks of C—O—C and C—H band at 1147 $cm^{-1}$ and 895 $cm^{-1}$.

Hyaluronic acid (HA) was oxidated by different concentrations of sodium periodate at room temperature. FIG. 1A shows the chemical reaction of HA oxidated by $NaIO_4$ to create two aldehyde functional groups. The FT-IR spectra of HA powder (i) and various degrees of oxidation of oxidated HA (oxi-HA) (low, middle and high degrees of oxidation of oxi-HA; (ii), (iii) and (iv), respectively) were shown in FIG. 1B. Significant peaks of aldehyde functional groups could be observed in the FT-IR spectra (ii, iii and iv) at 1725 $cm^{-1}$ and 836 $cm^{-1}$, the intensity of which increased as the degrees of oxidation increased (from ii to iv). The peaks at 1147 $cm^{-1}$ and 895 $cm^{-1}$ in the spectrum (i) of the HA powder were related to C—O—C (ether bond) and C—H. These two peaks were shifted to 1112 $cm^{-1}$ and 875 $cm^{-1}$, respectively, in the spectra (ii), (iii) and (iv) because of the formation of aldehyde functional groups.

The degree of oxidation of oxi-HA was further measured by t-BC titration (TNBS assay) as described previously. Table 1 summarized the theoretical degrees of oxidation calculated from the molar ratio of $NaIO_4$ and HA, and the obtained degree of oxidation measured by TNBS assay. As expected, the degree of oxidation of oxi-HA increased from 27.3±2.3% to 60.4±2.66% as the amount of $NaIO_4$ increased. The oxi-HA with a medium degree of oxidation (44.3±4.25%) was cross-linked by various concentration of ADH (2, 4 and 8 w/v %) in the following experiments.

TABLE 1

|  | Low oxi-HA | Middle oxi-HA | High oxi-HA |
| --- | --- | --- | --- |
| Molar ratio of HA and $NaIO_4$ | 1:0.5 | 1:1 | 1:2 |
| Theoretical oxidation degree | 50% | 100% | 100% |
| Oxidation degree (%)* | 27.30 ± 2.36 | 44.33 ± 4.25 | 60.40 ± 2.66 |
| Yield percentage (%) | 87.62 ± 2.94 | 84.04 ± 5.75 | 87.53 ± 4.42 |

Figure 2A:
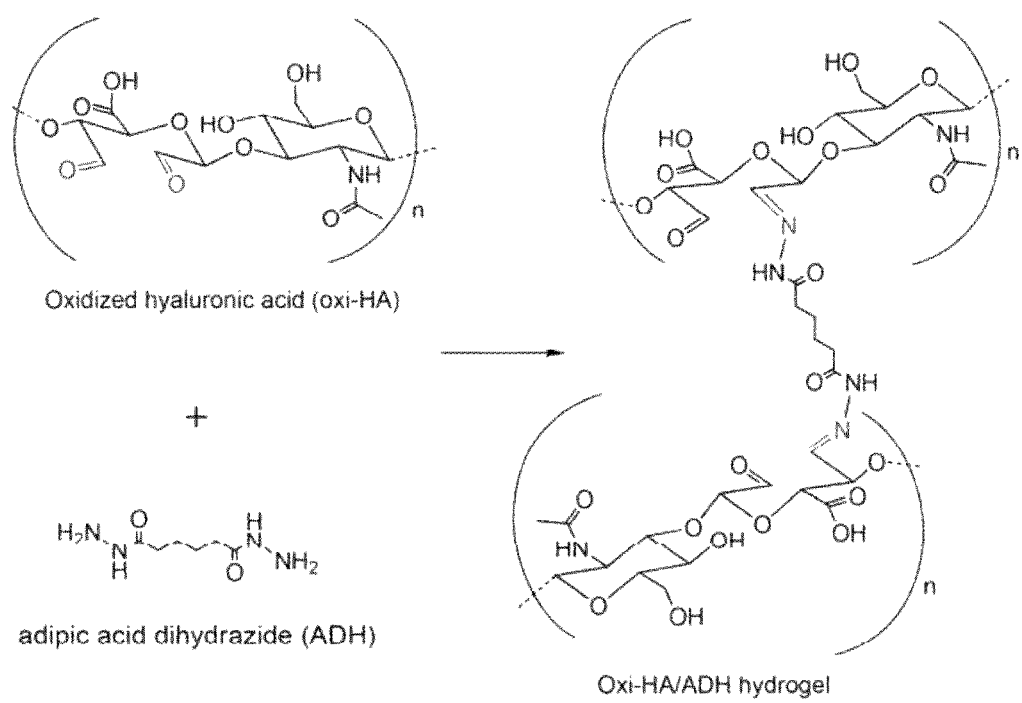
FIG. 2A is a schematic drawing showing oxi-HA covalently crosslinked with adipic acid dihydrazide (ADH).
Figure 2B:
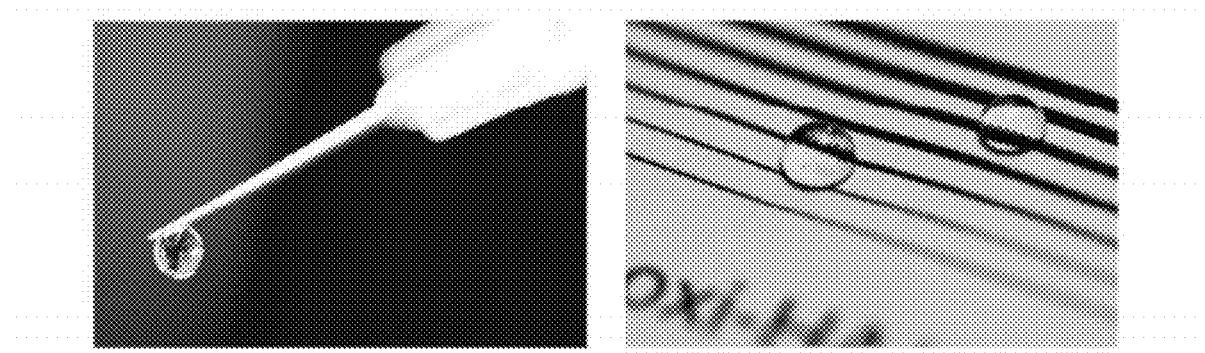
FIG. 2B shows oxi-HA/ADH solution could be injected through a 27-gauge needle (left panel) and form a colorless and transparent hydrogel (right panel).
Figure 2C:
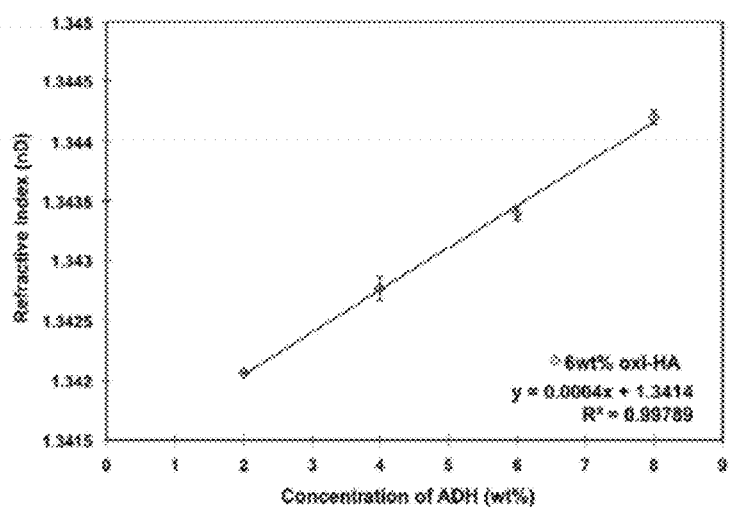
FIG. 2C shows refractive index of 6 w/v % oxi-HA (degree of oxidation: 44.3%) cross-linked with various concentrations of ADH (2 w/v % to 8 w/v %).

*oxidation degree was measured by TNBS assay 3.2. Refractive Index (RI) of Oxi-HA/ADH Hydrogel It was discovered that oxi-HA could be cross-linked with ADH, a bi-functional cross-linker, to form hydrogels without use of any chemical initiator. FIG. 2A shows the cross-linking reaction occurred spontaneously without the addition of any other chemical reagent to initiate the reaction. Aldehyde functional groups of oxi-HA reacted with the $NH_2$ functional group of ADH rapidly to form colorless, transparent oxi-HA/ADH hydrogel (FIG. 2B, left and right panels). The refractive index of the oxi-HA/ADH hydrogels ranged from 1.3420 to 1.3442 as the concentration of ADH was increased from 2% to 8% (FIG. 2C), which was close to that of human vitreous humor (1.3345~1.3348).

3.3. Rheological Properties of Oxi-HA/ADH Hydrogel

Oscillatory time sweeps were performed to evaluate the gelation behavior of oxi-HA/ADH hydrogel. FIG. 3 shows the elastic modulus (G') and viscous modulus (G") of oxi-HA/ADH2, oxi-HA/ADH4 and oxi-HA/ADH8 hydrogel at 4° C. and 37° C. The crossover point of G' and G" was defined as gel point which indicated the gel formation. The time required for the gel point to occur is sometimes referred to as the gelation time for the samples.

Figure 3A:
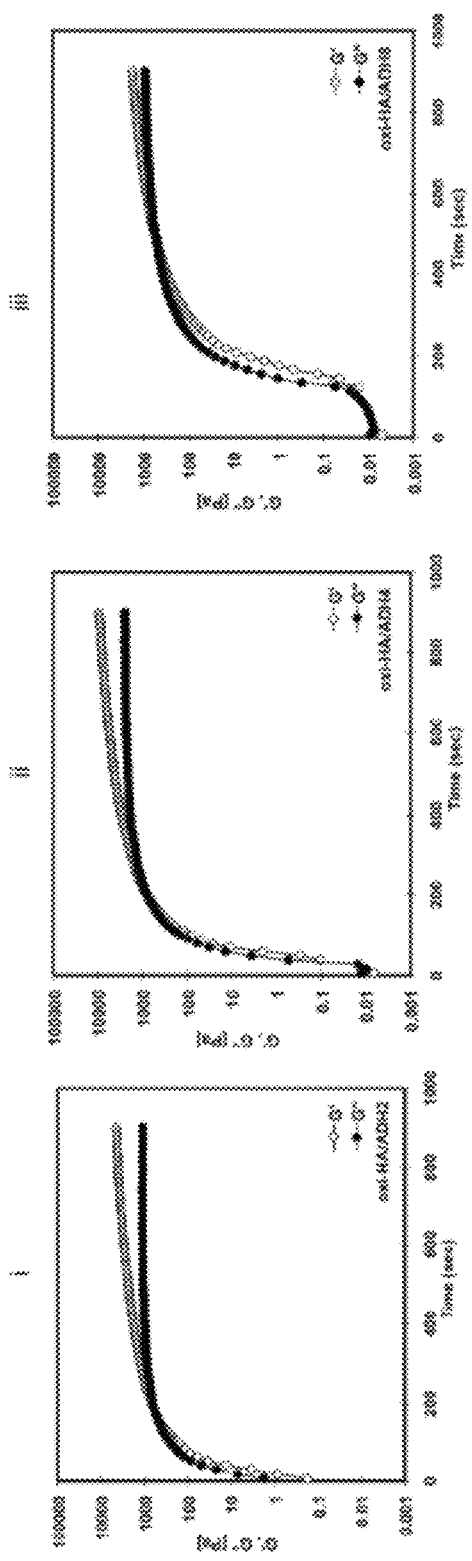
FIG. 3A is a graph showing the elastic (G', ○) and viscous (G", ●) moduli of oxi-HA/ADH hydrogel as a function of time at 4° C. The oxi-HA/ADH hydrogel was prepared by reacting 6% (wt/v) oxi-HA (DO 44.3%) with the cross-linker ADH 2% (i), 4% (ii) and 8% (wt/v) (iii), respectively. Elastic modulus (G', ○) and viscous modulus (G", ●) of oxi-HA/ADH hydrogel were measured at a constant frequency of 0.1 Hz as a function of time. The gel point is defined as the crossover point of G' and G". The time required for the gel point to occur is referred to as the gelation time.
Figure 3B:
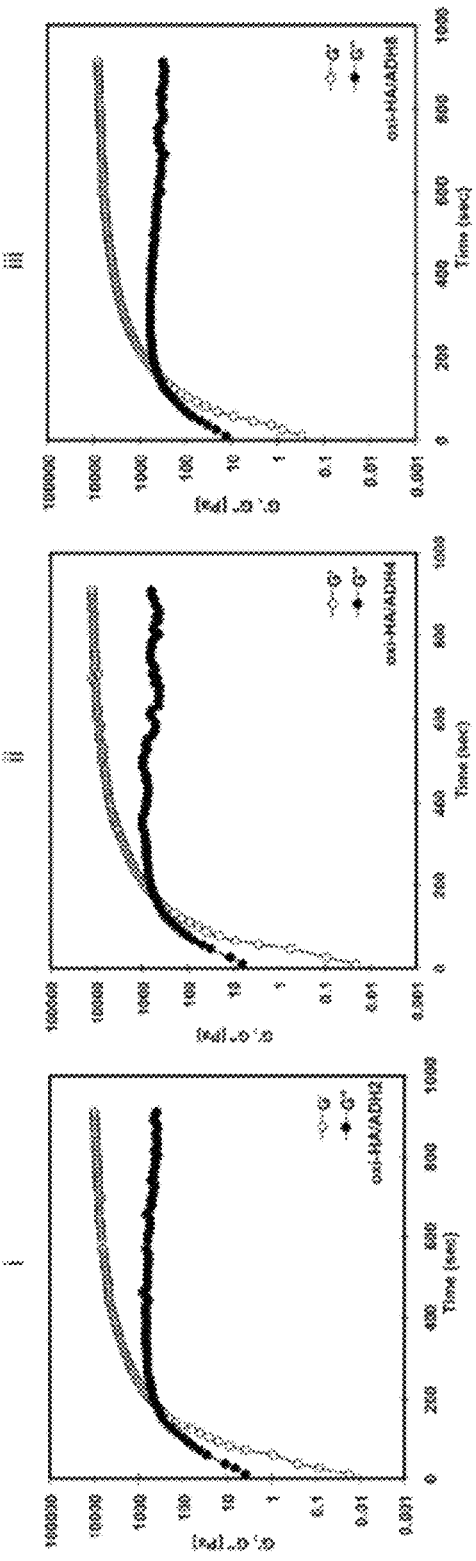
FIG. 3B is a graph showing the elastic (G', ○) and viscous (G", ●) moduli of oxi-HA/ADH hydrogel as a function of time at 37° C. The oxi-HA/ADH hydrogel was prepared by reacting oxi-HA with the cross-linker ADH as described in FIG. 3A.

FIG. 3A shows the rheological results of oxi-HA/ADH hydrogels (oxi-HA/ADH2, oxi-HA/ADH4 and oxi-HA/ADH8) at 4° C. These results indicate that all type of oxi-HA/ADH hydrogels can maintain in a liquid state at 4° C. for 3 to 8 min depending on the concentration of ADH in the hydrogel. FIG. 3B shows the rheological results of oxi-HA/ADH hydrogels at 37° C. The gel point of all hydrogels appears from 143 to 175 sec, which indicated that the oxi-HA/ADH hydrogels began to transform into a gel matrix within 3 min at 37° C. The results of rheological evaluation of oxi-HA/ADH hydrogels are summarized in Table 2.

TABLE 2

| Hydrogels | Refractive index (nD) | Gel point[a] (sec) 4° C. | Gel point[a] (sec) 37° C. | In-vitro degradation time |
| --- | --- | --- | --- | --- |
| Oxi-HA/ADH2 | 1.3420 ± 0.0000 | 180.3 | 175.4 | 2 days |
| Oxi-HA/ADH4 | 1.3427 ± 0.0001 | 202.2 | 158.7 | 14 days |
| Oxi-HA/ADH8 | 1.3442 ± 0.0001 | 491.7 | 143.4 | Over 35 days |

[a]the gel point was defined as the crossover point of G' and G" of rheological measurement (G' = G"); the time required for gel point to occur is referred to as gelation time.

3.4. In Vitro Degradation and Swelling Index of Oxi-HA/ADH Hydrogel

Figure 4:
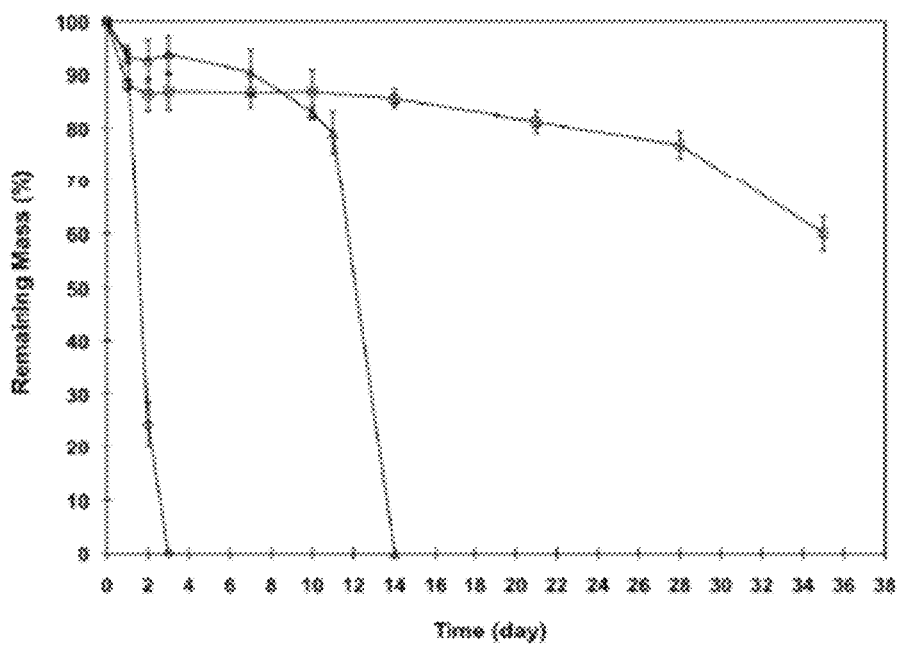
FIG. 4A is a graph showing the remaining mass of hydrogel after lysozyme digestion as a function of time. The oxi-HA/ADH hydrogel was prepared by reacting 6% (wt/v) of oxi-HA (DO 44.3%) with the cross-linker ADH 2% (◇), 4% (△) and 8% (wt/v) (□), respectively. The cylinder hydrogels (300 μl) were immersed in 3 ml of PBS containing 10,000 unit/ml of lysozyme.
FIG. 4B is a graph showing the swelling index of hydrogel after lysozyme digestion as a function of time. The oxi-HA/ADH hydrogel was prepared by reacting 6% (wt/v) oxi-HA (DO 44.3%) with the cross-linker ADH 2% (◇), 4% (△) and 8% (wt/v) (□), respectively.
Figure 4:
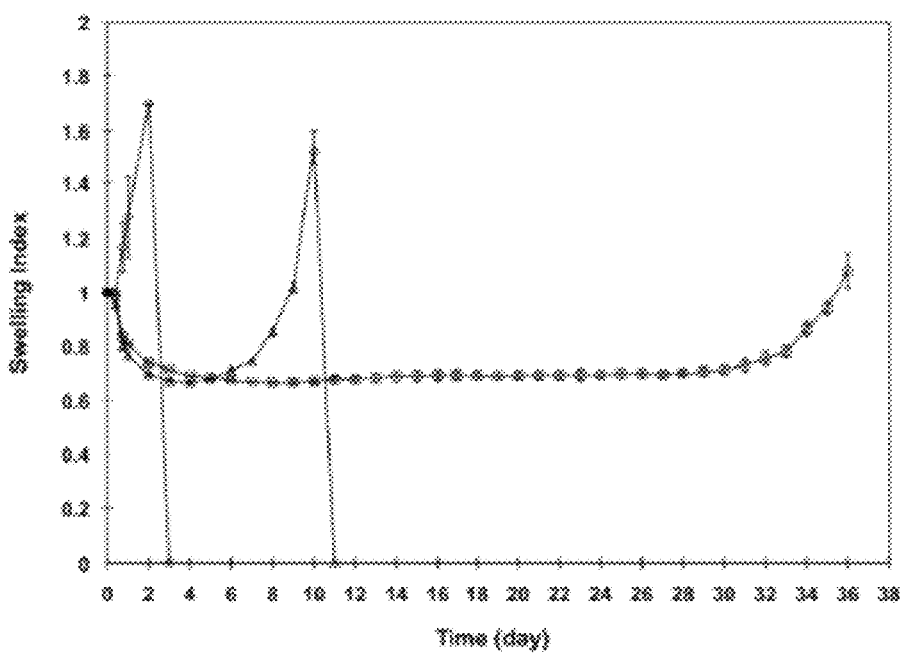

FIG. 4A shows the remaining mass of oxi-HA/ADH hydrogel in percentage as a function of time. The oxi-HA/ADH2 (◊) and oxi-HA/ADH4 (Δ) hydrogel were dissolved completely at Day 3 and Day 14, respectively. On Day 3, the remaining mass percentage of oxi-HA/ADH8 hydrogel (□) was 86.67±3.54%, which gradually decreased to 61.02±3.13% at Day 35. FIG. 4B shows the swelling index of oxi-HA cross-linked with different concentrations of ADH. The swelling index of oxi-HA/ADH2 hydrogel increased over time until the hydrogel was completely dissolved (within 3 days). The swelling index of oxi-HA/ADH4 and oxi-HA/ADH8 slightly decreased during the first 3 days and then maintained a constant value until the hydrogel began to degrade.

3.5 Cytotoxicity of Oxi-HA/ADH Hydrogel

Figure 5A:
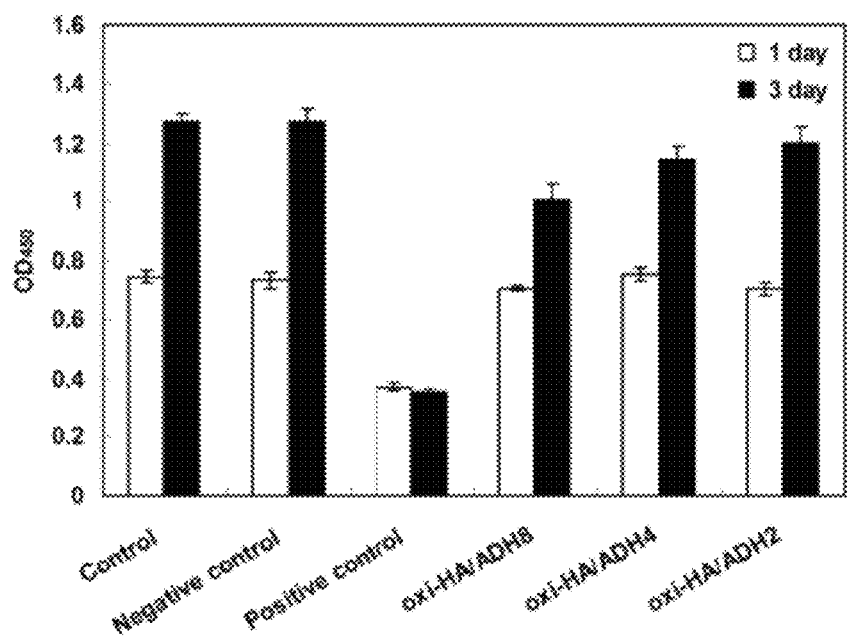
FIG. 5A is a graph showing oxi-HA/ADH hydrogels had no effect on cell proliferation. Optical density readings obtained in the WST-8 assay related to the cell proliferation (n=6).
Figure 5B:
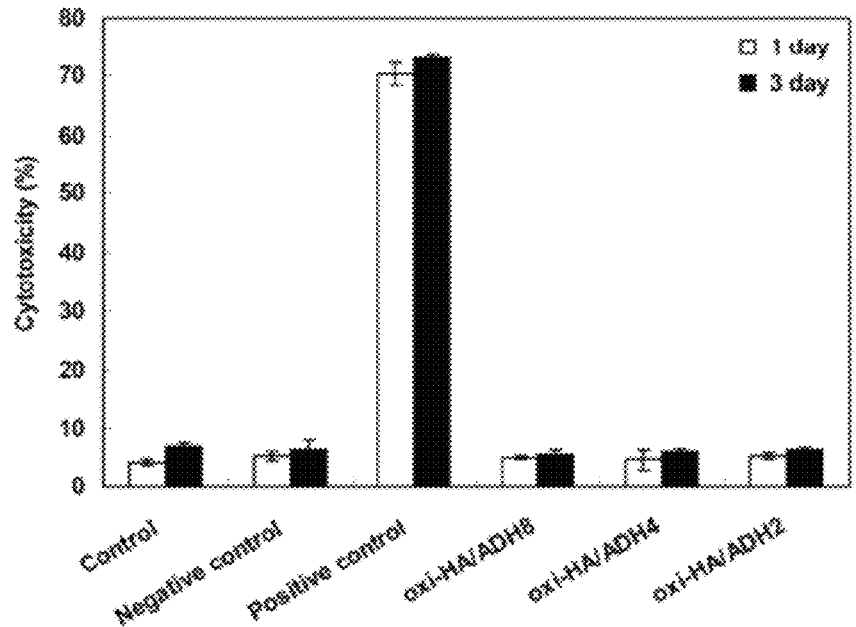
FIG. 5B is a graph showing oxi-HA/ADH hydrogels had no cytotoxic effect. The cells were cultured in the extraction medium of oxi-HA/ADH2, oxi-HA/ADH4 and oxi-HA/ADH8 hydrogel (n=6).

Cell viability was evaluated by WST-8 assay (FIG. 5A). There was no significant difference among the experimental groups (oxi-HA/ADH2, oxi-HA/ADH4 and oxi-HA/ADH8) on the first day ($p>0.5$). After culturing for 3 days, the WST-8 $OD_{450}$ values of the control, oxi-HA/ADH2, oxi-HA/ADH4 and oxi-HA/ADH8 groups were 1.27±0.03, 1.20±0.05, 1.14±0.04 and 0.99±0.06, respectively. The extraction medium of oxi-HA/ADH2 and oxi-HA/ADH4 ($p>0.5$) did not significantly influence the cell viability of RPE cell compared to the control and negative control group. However, the extraction medium of oxi-HA/ADH8 caused a small reduction in cell viability compared to the control group ($p<0.001$). The cytotoxicity was further examined by LDH assay (FIG. 5B) and showed that the cytotoxicity percentage of oxi-HA/ADH2, oxi-HA/ADH4 and oxi-HA/ADH8 were 6.1640±0.5805%, 6.0720±0.3872%, and 5.3166±0.9590%, respectively. The results showed that there was no significant difference among the oxi-HA/ADH extraction medium groups compared to the control group (6.9811±0.6663%, $p>0.5$).

Figure 6:
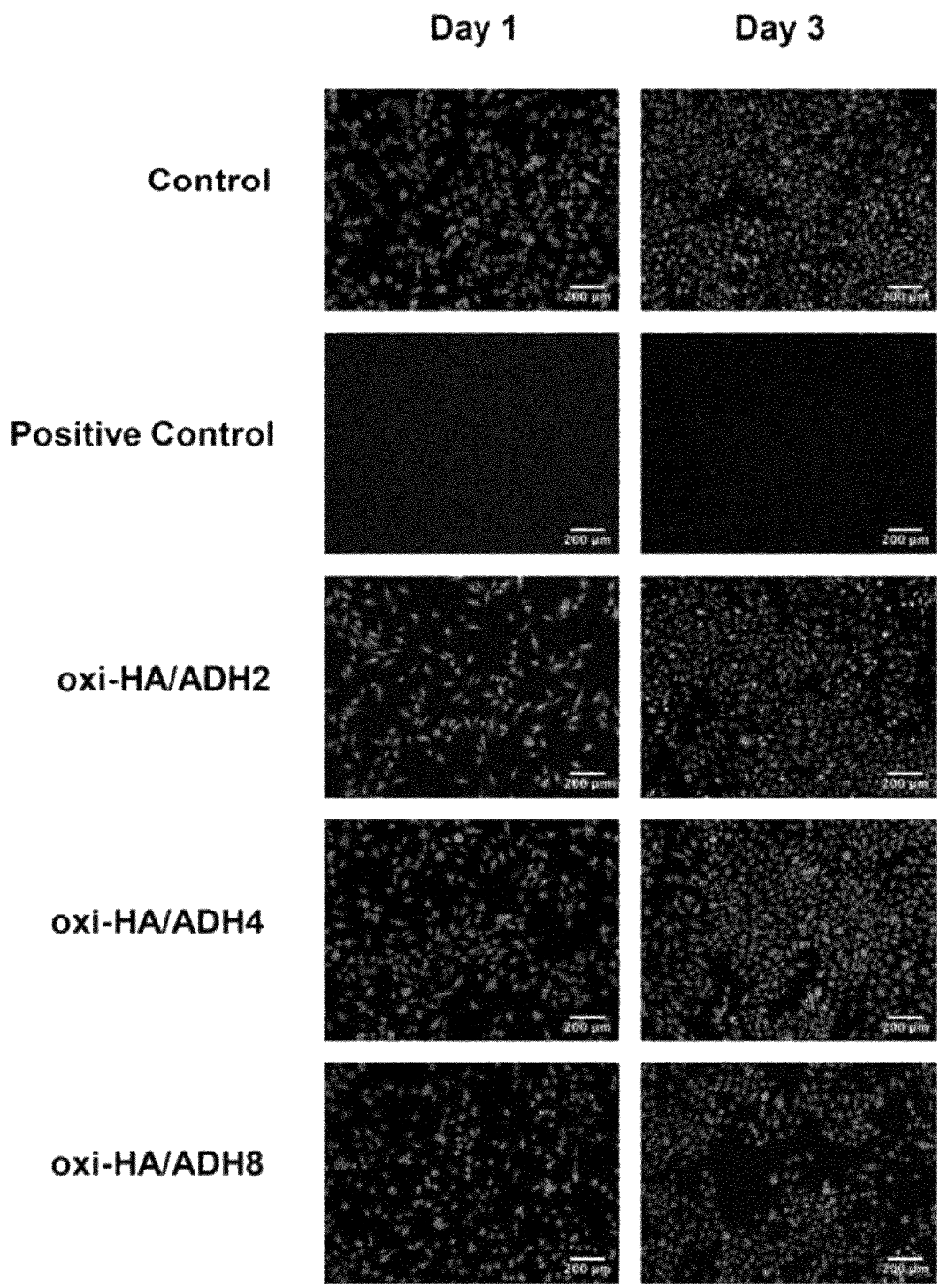
FIG. 6 is a collection of photomicrographs of cells stained with dyes for simultaneous detection of viable and dead cells in cell cultures with a fluorescent microscope. Magnification: 40×, scale bars 200 μm.

FIG. 6 shows fluorescent photomicrographs of the RPE cells cultured in the extraction medium of oxi-HA/ADH2, oxi-HA/ADH4 and oxi-HA/ADH8 hydrogel, respectively. The polyanionic dye calcein-AM can be retained within live cells and produces intense uniform green fluorescence in live cells. On the other hand, EthD-1 can enter cells with damaged membranes and produce bright red fluorescence in dead cells.

The results of live/dead cell staining demonstrated that most of the cells cultured in different extraction media were viable.

3.6 Preliminary Animal Study

Figure 7A:
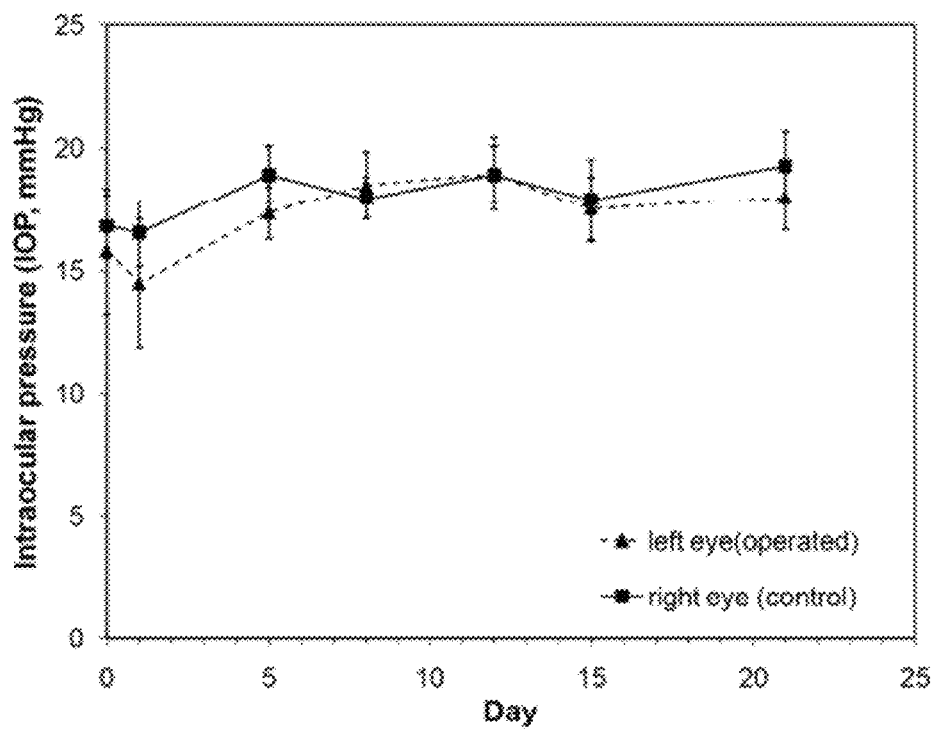
FIG. 7A shows no significant elevation of the intraocular pressure was observed during the observation period, and no significant differences were observed between the operated eyes and the control eyes.
Figure 7B:
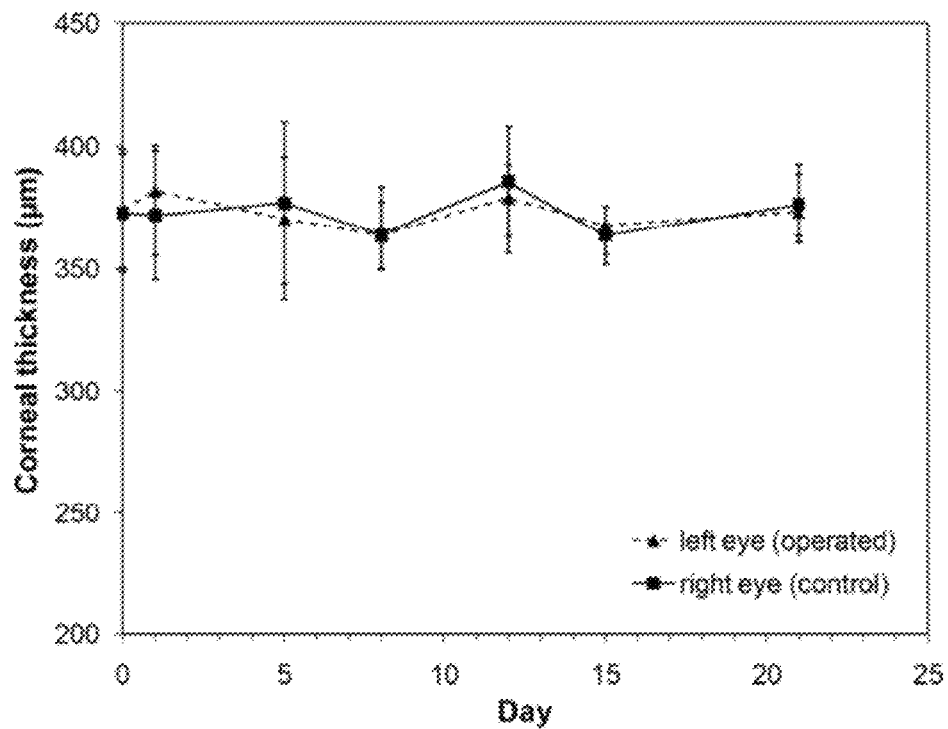
FIG. 7B shows no significant changes in the cornea thickness were observed throughout the observation period, and no significant differences were observed between the operated eyes and the control eyes were observed. (n=3)
Figure 8A:
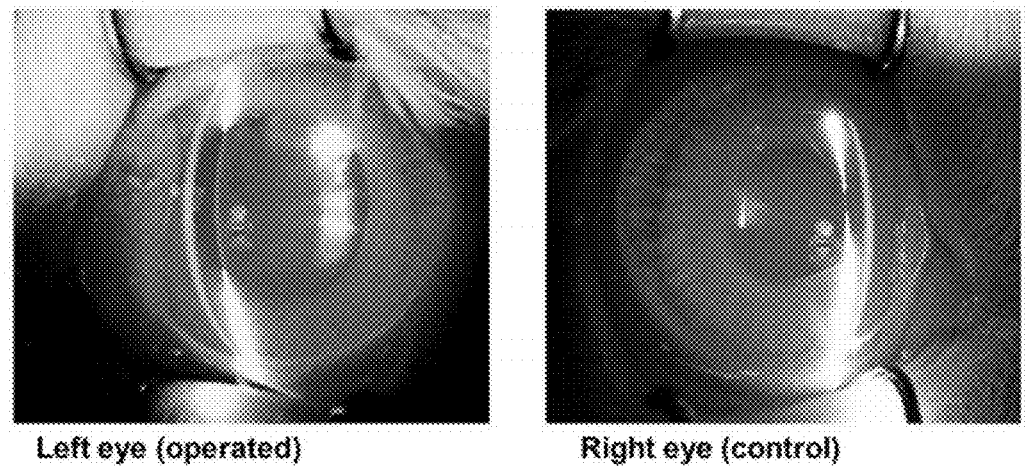
FIG. 8A shows a slit-lamp photograph of the oxi-HA/ADH8 injected eye (left) 3 weeks postoperatively and control eye (right).
Figure 8B:
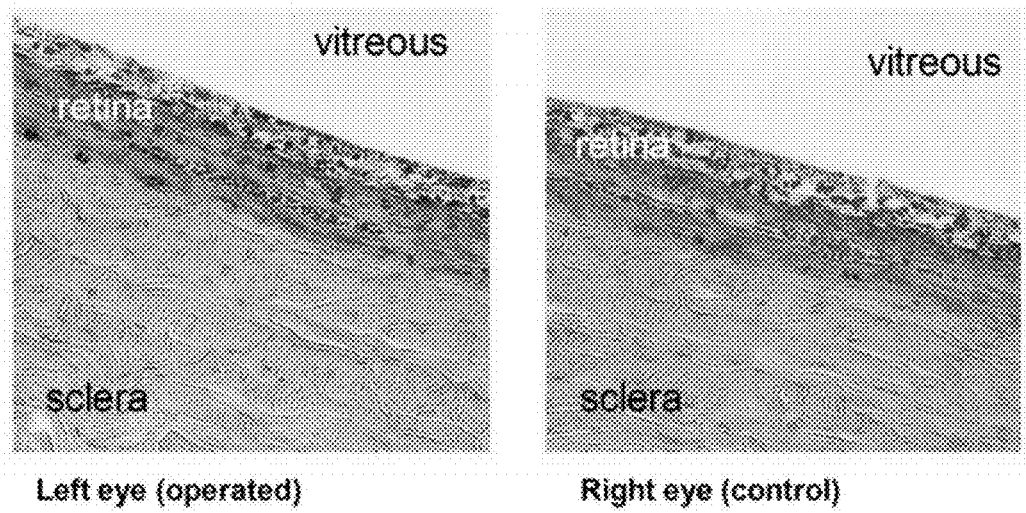
FIG. 8B shows a light microscope observation of retina histological section on day 21 after surgery (HE stain, 200×). Left: the operated eye; right: the control eye (right).

FIG. 7A showed changes in intraocular pressure (IOP) after operation. The IOP in operated eyes slightly decreased on postoperative day 1. There was an upward trend in IOP on day 5 and day 8 after the injection of oxi-HA/ADH hydrogel. On postoperative days 12, 15 and 21, IOP reached a plateau level. There was no significant difference in OP between the operated eyes and control eyes during the observation period. FIG. 7B showed cornea thickness of operated eyes and control eyes, and there were no significant difference in the cornea thickness between the groups. FIG. 8A showed photographs of slit lamp examinations of eyes on day 21 after the injection of oxi-HA/ADH8. The cornea and lens of operated eye presented no defect. The results revealed no significant inflammation or other disease in anterior segment of the eyes examined 3 weeks after the surgery. FIG. 8B showed retina sections of operated and control eyes 21 days after the surgery. The retinal layers were easily detected. There was no inflammatory reaction or infiltration, or any difference from the control eyes.

4. Discussion

When a patient undergoes vitrectomy surgery, much of vitreous humor is removed from the vitreous cavity. Because the natural vitreous is unable to regenerate, the vitreous cavity must be filled with a vitreous substitute to keep the retina in position and prevent it from detaching again. In past decades, development of vitreous substitutes has been a challenge for researchers. Many biopolymers and synthetic compounds have been examined in laboratories. However, ideal material for a permanent vitreous substitute has not been developed at present.

The discovery relates to a colorless and transparent oxi-HA/ADH hydrogel that can be injected into the vitreous cavity through a 27-gauge needle and subsequently transforms into a gel-like substance. The aldehyde functional groups on oxi-HA were created by $NaIO_4$, which cleaved the $C_2$-$C_3$ hydroxyl groups of glucurnonic acid to form dialdehyde, as characterized by FT-IR (peaks at 1725 $cm^{-1}$ and 836 $cm^{-1}$, FIG. 1B). The dialdehyde of oxi-HA could react with the hydrazide group of ADH to form intermolecular networks in oxi-HA/ADH hydrogel.

Refractive index is one of important optical characters for application of vitreous substitutes. An inappropriate refractive index of a vitreous substitute will influence the eyesight of a patient after vitrectomy surgery. Gases tamponade induce optical changes that are severe enough to limit temporally both the funduscopic examination and patient's eyesight. The refractive indices of current vitreous substitutes (e.g. silicone oil, nD=1.40516; heavy silicone oil, nD=1.3008) differ from that of the natural vitreous body (nD=1.336), induced refractive shifts in tamponade eyes are thus expected. The refractive index of oxi-HA/ADH8 is about 1.3342, which is quite similar to that of human vitreous body. The use of oxi-HA/ADH8 hydrogel as a vitreous substitute can avoid the undesired refractive changes after vitrectomy.

Clinically, injection through a small-gauge needle is the common procedure for delivery of a vitreous substitute. The oxi-HA/ADH8 hydrogel could be easily injected through a 27-gauge needle, as shown in FIG. 2B (left panel). The injectability is an important factor to ocular surgeons and patients. The operation time should be sufficient for an ocular surgeon to inject a liquid-state hydrogel into the vitreous cavity, and the time of solution-gel transformation should be as short as possible to prevent extrusion of hydrogel. The rheological evaluation showed that a mixture of oxi-HA solution and ADH solution could maintain in a solution form for about 8 minutes. Accordingly, ocular surgeons have sufficient time (8 min) to mix oxi-HA and ADH solution at 4° C. and then transfer the mixed oxi-HA/ADH solution into a syringe for injection. The liquid form can be injected and thus overcomes difficulties in introducing a substitute in a gel form and thus provides a minimally invasive delivery system for a vitreous substitute to the eye.

For a low cross-linked hydrogel (e.g., oxi-HA/ADH2), the swelling index increased immediately and dissolved completely within 3 days. During this time, the hydrogel undergoes hydrolysis and the hydrazone bonds were degraded almost linearly with time. For high cross-linked hydrogels (e.g., oxi-HA/ADH4 and oxi-HA/ADH8), the swelling index decreased during the first 3 days followed by a constant value and then increased until the networks were completely dissolved. The increase in the swelling index with time was a consequence of the hydrolysis of the hydrazone bonds in the hydrogel network. When hydrazone bonds in the hydrogel are hydrolyzed, the network swells and contains more water, and then dissolves completely. According to the mass loss studies, the degradation behavior found in oxi-HA/ADH4 and oxi-HA/ADH8 hydrogels was different from the one observed in oxi-HA/ADH2 hydrogels. Hydrogel with higher ADH content and therefore with higher number of hydrazone bonds, tend to hydrolyze slower than that with lower ADH content. In the high cross-linked hydrogels, there was an initial decrease in the mass loss (5-15%) for the first 3 days, likely due to the hydrolysis of the hydrogel regions with low cross-linking density or uncross-linked hyaluronic acid. This phase was followed by a slight decrease in the mass during the next few days or weeks, likely due to the degradation of high cross-linked regions. Finally, the hydrazone bonds in the hydrogel were hydrolyzed, which resulted in a dissolution phase.

The oxi-HA/ADH4 hydrogel showed a progressive swelling on 8-12 days, which meant that hydrazone bonds were hydrolyzed at this time, and then followed by a dissolution phase on 14 days. This resulted in a decrease in hydrogel mass and finally a complete dissolution of hydrogel. On the other hand, due to a high degree of cross-linking oxi-HA/ADH8 reached a constant swelling index for 3 days, and hydrogel showed a progressive swelling for 30-35 days. The in-vitro degradation experiments showed that only 30-40% of oxi-HA/ADH8 hydrogel was degraded in the presence of enzymes (PBS containing 10,000 unit/ml of lysozyme) and the hydrogel was stable for 5 weeks. Clinically, silicone oil and gases are the common vitreous substitutes in retina reattachment surgery to reestablish the intraocular volume and manipulate retina detachments. They prevent passage of fluid through retina breaks, maintain normal retina-retina pigment epithelium (RPE) apposition and maintain retinal reattachment. The longevity of gases is usually within a few days to 2 weeks, depending on the gas type, bubble volume, initial concentration and intraocular pressure. In contrast to intraocular gases, which reabsorb within few weeks, oxi-HA/ADH8 hydrogel can maintain gel matrix at least for 5 weeks in in-vitro degradation test. For clinical consideration, the longevity of oxi-HA/ADH8 hydrogel should be beneficial for retina attachment. Furthermore, the hydrogel overcomes the inconvenience of face-down position when patients undergo the vitrectomy with gases tamponade.

Retina pigmented epithelium (REP) cells were selected as target cell for cytotoxicity evaluation because it is often exposed directly to the vitreous substitute filling the globe after retina detachment or local retinectomy. RPE cells were also found to be associated with failed retinal reattachment and proliferative vitreoretinopathy (PVR). The cell viability assays (WST-8) and cytotoxicity (LDH assay) indicate that oxi-HA/ADH hydrogel was biocompatible and non-toxic with RPE cells in in-vitro evaluation. Degradation products of hydrogel are another concern for clinical application. According to the results of degradation evaluation, oxi-HA/ADH2 hydrogel was degraded within 3 days in aqueous environments. This indicates that oxi-HA/ADH2 hydrogel totally degraded in the extraction medium during extraction process (37° C., 72 hr) and the degraded products were cultured with RPE cell in cytotoxicity evaluation. According to the cytotoxicity assay data (FIGS. 5A-5B), there was no significant cytotoxicity in this group. These results indicated that the degradation products from oxi-HA/ADH hydrogel were non-cytotoxic to RPE cells based on WST-8 and cytotoxicity assay. In addition, live/dead staining also demonstrates that most of the cultured cells from different extraction medium were viable.

Slit-lamp examination of oxi-HA/ADH8 injected eyes revealed no findings of inflammation or opacity in the anterior ocular segment during observation period. An increase in IOP often occurs after vitrectomy surgery. However, IOP of operated eyes remained at normal level during the observation period. This may be due to a slightly decrease in swelling index of oxi-HA/ADH hydrogel. Histological examination of the retina tissue also showed no structure changes or degradation, and also no significant difference from the control eyes.

5. Conclusion

Currently, ideal vitreous substitutes have not been developed yet for clinical applications. Many researches made efforts toward developing appropriate biomaterials for vitreous substitutes. The invention relates to synthesis and characterization of a novel injectable hyaluronic acid-based hydrogels, oxi-HA/ADH. The hydrogel displays several beneficial properties for use as a vitreous substitute, such as appropriate refractive index, injectable and in-situ gelling properties and showing no cytotoxicity to REP cells. Additionally, the oxi-HA/ADH8 hydrogel was not degraded in vitro by ocular enzyme (lysozyme) over 5 weeks. In the preliminary animal study, the oxi-HA/ADH hydrogel induced no serious complication during the observation period.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of replacing the vitreous of an eye comprising:
providing a first solution comprising oxidated hyaluronic acid;
providing a second solution comprising a dihydrazide;
admixing the first and second solutions to form a composition comprising a polymer comprising the oxidated hyaluronic acid cross-linked by the dihydrazide, wherein the polymer is a hydrogel exhibiting the following properties:
(a) transparent and colorless; and
(b) transforming from a liquid state into a gel-matrix at 37° C.;
removing the vitreous from a vitreous cavity of an eye;
replacing the vitreous with air; and
injecting into the vitreous cavity the composition in an amount sufficient to replace the air.

2. The method of claim 1, wherein the dihydrazide is at least one chose from adipic acid dihydrazide, oxalyldihydrazide, succinic dihydrazide, malonic dihydrazide, ethylmalonic acid, dihydrazide, sebasic acid dihydrazide, isophthalic acid dihydrazide, Ajicure LDH, Ajicure VDH, maleic acid dihydrazide and pimelic acid dihydrazide.

3. The method of claim 1, wherein the cross-linked, oxidated hyaluronic acid of the polymer comprises glucuronic acids with C2 or C3 or both thereof being aldehyde groups.

4. The method of claim 1, wherein the dihydrazide cross-links two chains of oxidated HA via C2 and C3 of glucuronic acids of the oxidated HA.

5. The method of claim 1, wherein the weight ratio between the oxidated HA and the hydrazide in the hydrogel polymer ranges from 12:1 to 3:1.

6. The method of claim 1, wherein the weight ratio between the oxidated HA and the hydrazide is 3:1.

7. The method of claim 1, wherein the composition has a refractive index ranging from 1.341 to 1.345.

8. The method of claim 1, wherein the admixing step is performed at a temperature that forms a polymer having a gelation time of at least 3 minutes.

9. The method of claim 1, wherein the concentration of the oxidated hyaluronic acid in the first solution is greater than 4% but less than (w/v) 8%, and wherein the concentration of the dihydrazide in the second solution ranges from 2 to 8%.

10. The method of claim 1, wherein the polymer comprises a structure of formula (I):

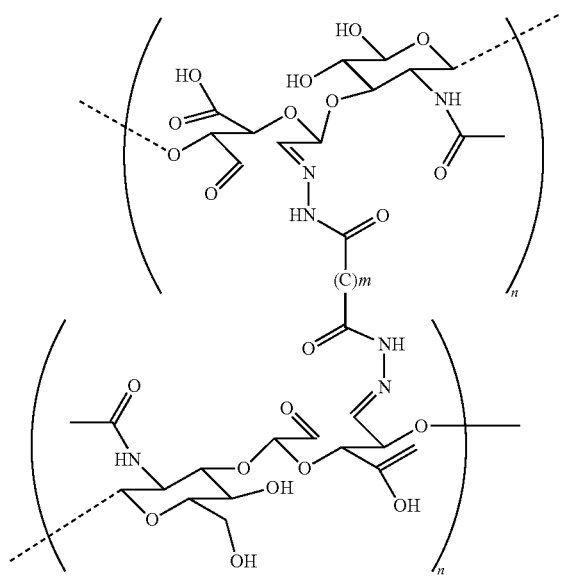

wherein m, n are integers, m≦5, 100≦n≦2500 and the polymer is a hydrogel.

11. The method of claim 10, wherein m=4.

12. A method of replacing the vitreous of an eye in an animal comprising:
   removing the vitreous from a vitreous cavity of the eye in the animal;
   replacing vitreous with air; and
   injecting into the vitreous cavity of the eye a sufficient amount of a composition comprising a hyrogel polymer, the hydrogel polymer comprising:
      (a) oxidated hyaluronic acid; and
      (b) a dihydrazide, the dihydrazide cross-linking the oxidated hyaluronic acid;
   wherein the hydrogel polymer exhibits the following properties:
      (i) transparent and colorless; and
      (ii) transforming from a liquid state into a gel-matrix at 37° C.,
   wherein the composition has a refractive index ranging from, 1.341 to 1.345, and the weight ratio of oxidated hyaluronic acid and dihydrazide is 3:1.

13. A method of replacing the vitreous of an eye comprising:
   removing the vitreous from a vitreous cavity of an eye;
   replacing the vitreous with air; and
   injecting into the vitreous cavity an amount of a composition comprising a polymer, the polymer comprising oxidated hyaluronic acid cross-linked by a dihydrazide, wherein the amount of the composition is sufficient to replace the air and the polymer is a hydrogel exhibiting the following properties:
      (a) transparent and colorless; and
      (b) transforming from a liquid state into a gel-matrix at 37° C.

14. The method of claim 13, wherein the composition has a refractive index ranging from 1.341 to 1.345.

15. The method of claim 13, wherein the weight ratio of oxidated hyaluronic acid and dihydrazide in the composition is 3:1.

16. The method of claim 13, wherein the weight ratio between the oxidated HA and hydrazide in the hydrogel polymer ranges from 12:1 to 3:1.

17. The method of claim 13, wherein the polymer comprises a structure of formula (I):

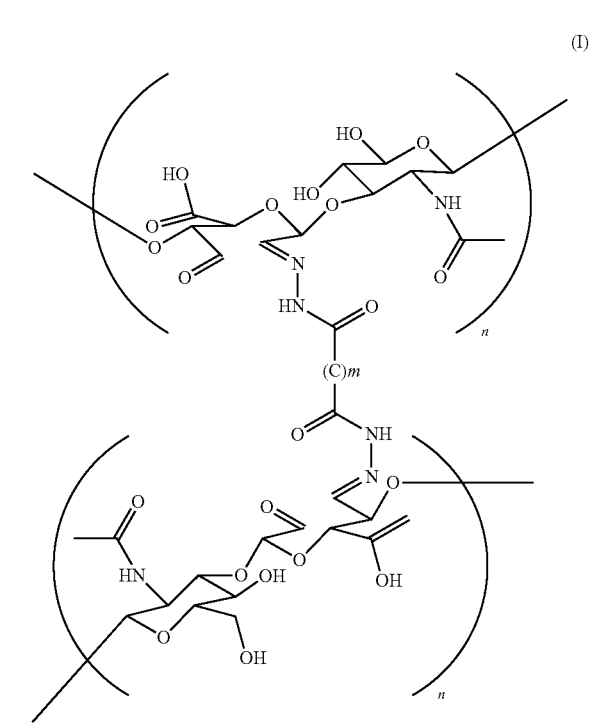

wherein m, n are integers, m≦5, 100≦n≦2500 and the polymer is a hydrogel.

18. The method of claim 17, wherein m=4.

19. The method of claim 13, wherein the dihydrazide is at least one chosen from adipic acid dihydrazide, oxalyldihydrazide, succinic dihydrazide, malonic dihydrazide, ethylmalonic acid, dihydrazide, sebasic acid dihydrazide, isophthalic acid dihydrazide, Ajicure LDH, Ajicure VDH, maleic acid dihydrazide and pimelic acid dihydrazide.

20. The method of claim 13, wherein the dihydrazide is adipic acid dihydrazide.

\* \* \* \* \*